United States Patent [19]

Groegler et al.

[11] 4,001,232

[45] Jan. 4, 1977

[54] PROCESS FOR PREPARING 1-SUBSTITUTED 2-METHYL-TETRAHYDROPYRIMIDINES

[75] Inventors: Gerhard Groegler, Leverkusen; Gerhard Dankert; Klaus Recker, both of Cologne; Josef Backes, Dormagen, all of Germany

[73] Assignee: Bayer Aktiengesellschaft, Leverkusen, Germany

[22] Filed: July 22, 1975

[21] Appl. No.: 598,083

[30] Foreign Application Priority Data

Aug. 17, 1974 Germany .................... 2439550

[52] U.S. Cl. .................. 260/251 R; 260/561 R; 260/479 S; 260/482 R; 260/561 A; 260/562 N
[51] Int. Cl.$^2$ ...................................... C07D 239/06
[58] Field of Search ................ 260/251 R

[56] References Cited

OTHER PUBLICATIONS

Brown; "The Pyrimidines", pp. 445–448 (1962).
Chem. Ber., 98, 3652–3659 (1965).

*Primary Examiner*—Lewis Gotts
*Assistant Examiner*—D. R. Phillips
*Attorney, Agent, or Firm*—Burgess, Dinklage & Sprung

[57] ABSTRACT

1-substituted 2-methyl-tetrahydropyrimidines are prepared by reacting an N-substituted propylene diamine with an acetoacetic acid ester or amine at a temperature of from 0° to 80° C and removing the water produced in the reaction at a temperature of from 0° to 80° C.

7 Claims, No Drawings

PROCESS FOR PREPARING 1-SUBSTITUTED 2-METHYL-TETRAHYDROPYRIMIDINES

BACKGROUND

The present invention relates to a new process, which can also be carried out on an industrial scale, for the preparation of 1-substituted 2-methyl-tetrahydropyrimidines from N-substituted propylenediamines and acetoacetic acid esters or acetoacetic acid amides.

A range of other processes for the preparation of 1-alkyl-2-methyl-tetrahydropyrimidines has already been disclosed, such as, for example, the reaction of N-alkylpropylenediamines with open-chain imide-acid esters or amidines (A. Pinner, Die Chemie der Imidoather und ihrer Derivate, (The Chemistry of the Imido-ethers and of their Derivatives), R. Oppenheim, Berlin, 1892), the reaction of N-alkyl-propylenediamine-toluenesulphonic acid salts with carboxylic acid nitriles (J.Chem.Soc. 1947, 497), the hydrogenation of N-acylamino-nitriles, in which the N-acyl-N-alkyl-propylenediamines formed are dehydrated under the reaction conditions to give 1-alkyl-2-methyl-tetrahydropyrimidines (J.Am.Chem.Soc. 71, 2350 (1949)) and the reaction of N-alkylpropylenediamines with oxazolines (German Published Specification No. 2,154,948).

However, many of these processes have the disadvantage that the reaction does not take place completely and, in particular, large amounts of undesired by-products are formed. The reaction temperature in these known processes of preparation is throughout 100°–200° C and the reactions are carried out in the presence of catalysts, for example acid compounds (hydrochloric acid or toluenesulphonic acid) or metal compounds (Ni, Co and Cu).

Further, the reaction of N-ethyl-propylenediamine with acetoacetic acid ethyl ester (Chem. Ber. 98, 3652 (1965)) in the presence of toluenesulphonic acid at reaction temperatures of 210° C is known. This process has been described for an 0.2 molar reaction batch which cannot, however, be extended to industrial scales. Tetrahydropyrimidines, being cyclic amidines, are extremely prone to hydrolysis, so that at the temperature mentioned and in the presence of acid compounds, such as toluenesulphonic acid, the cyclic amidine is immediately saponified by the water formed during the condensation. The N-acyl-N-ethyl-propylenediamine produced by saponification can admittedly be recycled slowly, with elimination of water, under the conditions prevailing in the process of working up by distillation; this recycling is realisable within an entirely acceptable space of time in the case of an 0.2 molar batch, but gives a totally unsatisfactory space-time yield when this process is carried out industrially in batches of 100 kg or more. The working up of the resulting ternary mixture of tetrahydropyrimidine, its saponification product N-acyl-N-alkylpropylenediamine and water proves to be very costly and requires a time-consuming and involved distillation technique. In addition, in consequence of the heat exposure of the reaction mixture, a very high proportion of inutilisable residues is obtained, which substantially lowers the yield of pure product (compare Example 1).

SUMMARY

Broadly in accordance with this invention 1-substituted, 2-methyltetrahydropyrimidines are prepared by reacting an N-substituted, propylene diamine with an acetoacetic acid ester or amide at a temperature of from 0° to 80° C, and removing the water produced in the reaction at a temperature of from 0° to 80° C.

More specifically, the present invention provides a process for the preparation of a 1-substituted 2-methyl-tetrahydropyrimidine of the general formula

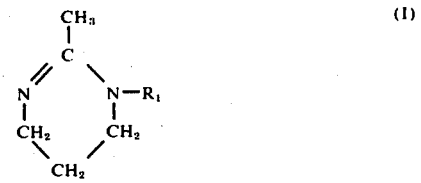

in which
$R_1$ denotes a straight-chain, branched-chain or cyclic, saturated, unsaturated or aromatic, optionally substituted hydrocarbon radical with from 1 to 17 carbon atoms which comprises reacting an N-substituted propylenediamine of the general formula

in which
$R_1$ has the abovementioned meaning
with an acetoacetic acid derivate of the general formula

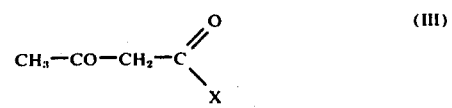

in which
X represents $-OR_2$, $-NHR_2$ or $-N(R_2)_2$ and
$R_2$ represents an optionally substituted aryl, alkyl or cycloalkyl radical with $1 - 17$ C atoms
at a temperature of from 0° to 80° C, and removing the water produced in the reaction at a temperature of from 0° to 80° C. The process may be carried out in the absence of a catalyst.

The process according to the invention can be illustrated by the following equation.

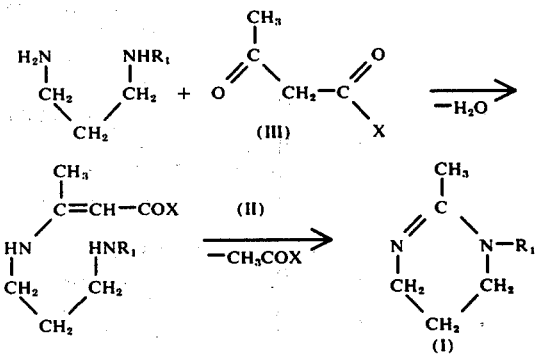

In this equation, $R^1$ and X have the same meaning as mentioned above.

DESCRIPTION

The condensation product of the amine employed and the acetoacetic acid derivative employed, which arises as an intermediate product, can in some cases be isolated. However, under the conditions indicated, the reaction takes place effortlessly through to the 1-substituted 2-methyltetrahydropyrimidine.

The N-substituted propylenediamines to be employed in the process according to the invention can be substituted in the radical $R_1$, for example by one or more CN, halogen or OH groups. Preferably, N-substituted propylenediamines in which $R_1$ has 1 – 6 or 12 – 17 C atoms are employed. N-substituted propylenediamines in which $R_1$ denotes a straight-chain and saturated hydrocarbon radical are also preferred. The following individual compounds may be mentioned as examples: N-methyl-1,3-propylenediamine, N-ethyl-1,3-propylenediamine, N-n-butyl-1,3-propylenediamine, N-octyl-1,3-propylenediamine, N-dodecyl-1,3-propylenediamine, N-stearyl-1,3-propylenediamine, N-β-hydroxyethyl-1,3-propylenediamine, N-cyclohexyl-1,3-propylenediamine, N-benzyl-1,3-propylenediamaine and N-phenyl-1,3-propylenediamine.

Acetoacetic acid derivatives which can be used for the process according to the invention are acetoacetic acid esters and monosubstituted or disubstituted acetoacetic acid amides. Within the general formula

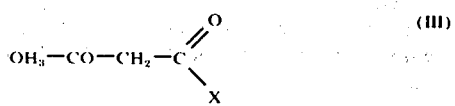

preferred acetoacetic acid derivatives are those in which X represents $-OR_2$, $-NHR_2$ or $-N(R_2)_2$ and $R_2$ denotes a saturated alkyl, cycloalkyl or aryl radical with 1 – 7 C atoms. Acetoacetic acid esters ($X = OR_2$), in which $R_2$ represents a saturated alkyl or cycloalkyl radical with 1 – 6 C atoms are very particularly preferred.

The following individual compounds may be mentioned as examples of acetoacetic acid derivatives which can be employed: acetoacetic acid methyl ester, acetoacetic acid ethyl ester, acetoacetic acid butyl ester, acetoacetic acid benzyl ester, acetoacetic acid phenyl ester, acetoacetic acid N-methylamide, acetoacetic acid N-diethylamide, acetoacetic acid N-butylamide, acetoacetic acid N-dipropylamide, acetoacetic acid N-benzylamide, acetoacetic acid N-cyclohexylamide and acetoacetic acid N-phenylamide.

The acetoacetic acid derivatives which can be employed in the process according to the invention are easily accessible in a known manner, by reaction of diketene with the corresponding alcohols or N-monosubstituted or N-disubstituted amines.

In general, the process according to the invention is carried out as follows: either the N-substituted propylenediamine employed is first taken and the acetoacetic acid derivative is added, or the acetoacetic acid derivative is first taken and the N-substituted propylenediamine is added. The process can be carried out in the presence or absence of a solvent. The reaction temperature is set to 0° – 80° C. The water produced in the reaction is removed, again at 0° – 80° C, and this can be effected by addition of a dehydrating agent which is inert towards the starting materials and the reaction products, or by distillation, if appropriate under reduced pressure, or by azeotropic distillation, if appropriate under reduced pressure. The working up of the residual reaction mixture to isolate 1-substituted 2-methyltetrahydropyrimidine is carried out in a manner which is in itself known, for example by distillation or extraction.

Suitably, the starting compounds are employed in the stoichiometric molar ratio. However it can also be advantageous to employ one of the starting compounds in excess, for example in an excess of up to 1.5 mols per mol of the second starting compound.

The process is preferably carried out in the presence of a solvent. Suitably, the solvent should be inert towards the starting materials and reaction products. Examples of solvents which can be used are halogenohydrocarbons, aromatic hydrocarbons, esters, preferably esters of aliphatic monocarboxylic acids with aliphatic alcohols or aliphatic diols, such as methyl acetate, ethyl acetate, butyl acetate, ethyleneglycol acetate and ethyleneglycoldiacetate, and ethers, preferably aliphatic ethers such as diethyl ether, dipropyl ether and ethylene glycol dimethyl ether, and cyclic ethers such as tetrahydrofurane and dioxane. It is preferred to use inert solvents together with which the water produced in the reaction can also subsequently be distilled off azeotropically. Accordingly, it is possible to employ, with advantage, those inert solvents which boil below 150° C under normal pressure and form an azeotrope with water. Such solvents can be, for example, halogenohydrocarbons and aromatic hydrocarbons. Methylene chloride, chloroform, dichloroethane, trichloroethane, benzene, toluene, xylene and chlorobenzene may be mentioned as examples.

The reaction temperature in the process according to the invention is preferably set to 10° – 70° C, very particularly preferentially to 20° – 50° C. The removal of the water produced in the process according to the invention is preferably effected at 10° – 70° C, and very particularly preferentially at 20° – 50° C. As already mentioned, the removal of water can be effected, for example, by distillation, azeotropic distillation or addition of an inert dehydrating agent.

If the water of reaction is removed by distillation, this distillation is preferably carried out in vacuo, so that the temperatures can be kept below 80° C whilst removing the water. For example, pressures of 10 – 700 mm Hg can be employed.

Where the water of reaction is to be removed by addition of an inert dehydrating agent, the latter is suitably added in at least such amount that the theoretically calculated amount of water produced can be found. Advantageously, an excess of dehydrating agent is employed. Examples of suitable dehydrating agents are anhydrous sodium carbonate, anhydrous (calcined) sodium sulphate, barium oxide and calcium oxide, zeolites and molecular sieves based on organic polymers.

Preferably, the water is removed by azeotropic distillation using one of the azeotrope-forming solvents already described. If the azeotropic distillation is carried out discontinuously, the azeotrope-forming solvent is suitably added in at least such amount that the theoretically calculated amount of water of reaction produced can be removed. Preferably, an excess of azeotrope-forming solvent is used. If the azeotropic distillation is carried out continuously, it is also possible to use less azeotrope-forming solvent. In this case, after cooling and phase separation of the azeotrope which has been distilled off, the aqueous phase is removed and the azeotrope-forming solvent is recycled. This circulation is then maintained until no further water is removed from the reaction mixture. The pressure conditions to be maintained during removal of the water of reaction by azeotropic distillation depend on the azeotrope formed. The pressure is so chosen that the temperature (measured in the reaction mixture) does not rise above 80° C during the azeotropic distillation. Where azeotropes are formed which boil below 80° C under normal pressure, the process can be carried out under normal pressure or under reduced pressure. Suitable pressures in such a case are, for example, from 10 mm Hg to normal pressure, especially from 15 to 50 mm Hg. If azeotropes having a boiling point above 80° C under normal pressure are formed, the process must be carried out under reduced pressure. Suitable pressures in such a case are, for example, from 10 to 200 mm Hg, especially from 15 to 50 mm Hg.

The 1-substituted 2-methyl-tetrahydropyrimidine is preferably isolated by distillation from the mixture now present. The pressure at which this distillation is carried out can be varied within wide limits since now temperatures above 80° C can also arise without causing side-reactions to take place to a significant extent. For example, it is possible to employ such pressures that the 1-substituted 2-methyl-tetrahydropyrimidine to be isolated boils at between 0° and 200° C. Preferably, the distillation is carried out under normal pressure or reduced pressure, for example at 0.05 – 760 mm Hg. Pressures of about 0.1 – 50 mm Hg, and a boiling point, of the 1-substituted 2-methyltetrahydropyrimidine to be isolated, in the range from 70° to 170° C, are particularly preferred.

Whilst the process according to Chem.Ber. 98, 3652 (1958) is carried out at a high temperature and in the presence of toluenesulphonic acid as the catalyst, with the water of reaction remaining in the reaction mixture for a relatively long time, the process according to the invention is based on the fundamental invention that high yields of 1-substituted 2-methyl-tetrahydropyrimidines are only obtained if the process is carried out at low temperatures and without catalyst. In addition, it has been found that the water of reaction must be withdrawn from the reaction batch at a low temperature to prevent hydrolysis of the cyclic amidine.

The advantages achievable with the process according to the invention reside above all in the fact that 1-substituted 2-methyl-tetrahydropyrimidines can be prepared more simply and in better yield, even on an industrial scale, than hitherto, and that the starting components are extremely easily accessible. The process according to the invention can also, without difficulties, be carried out continuously.

The 1-substituted 2-methyl-tetrahydropyrimidines which can be prepared according to the invention can be used as catalysts in the isocyanate-polyol addition reaction (compare Published Japanese Patent Application No. 71/02,672).

Furthermore they can be used as intermediates for preparing pharmaceuticals (see Br. J. Pharmac., vol. 37 (1969), p. 425), as compounds for the anti-electrostatic finish of polyolefines (compare German published Applications 2,103,145 and 2,152,949) and for preparing adhesive sompositions (see Japanese published application 25138/72). Furthermore they can be used as catalysts in chemical reactions e.g. the Michael-addition and as hydrogen halogenide acceptors.

The invention will now be illustrated on the following Examples:

EXAMPLE 1 (COMPARISON EXAMPLE)

In transferring the known process of preparation of 1-alkyl-2-methyl-tetrahydropyrimidines, according to Chem. Ber. 98, 3652 (1965), to an industrial scale, the following results were obtained:

A mixture of 260 kg (2 kmols) of acetoacetic acid ethyl ester, 176 kg (2 kmols) of N-methyl-propylenediamine and 2.2 kg of toluenesulphonic acid was heated to 170° C over the course of 10 hours. During this time, 151 kg (calculated amount = 176 kg) of ethyl acetate and 9 kg (calculated amount = 36 kg) of water gradually distil over. The balance of the amounts of ethyl acetate and water eliminated already indicates that, whilst under these conditions 86% of the ethyl acetate is liberated, only about 25% of the calculated amount of water is liberated. The missing proportion of about 75% of the total amount of water reacts with the cyclic amidine formed, causing saponification, so that under these conditions acetoacetic acid ethyl ester and N-methyl-propylenediamine mainly form N-acyl-N-methyl-propylenediamine and not the cyclic amidine. On working up the reaction mixture by distillation, recyclisation of the N-acyl-N-methyl-propylenediamine gradually occurs, in part with renewed elimination of water, and 188 kg of a crude mixture, of only 60% purity with respect to 1,2-dimethyl-tetrahydropyrimidine are obtained (water content = 6 – 7%, N-acyl-N-methyl-propylenediamine 8 – 10%). The unusable residue amounts to 90 kg, which is disproportionately high. Because of the difficulty of separating the crude mixture, the purification can only be effected by carrying out a distillative separation at a vacuum of about 20 mm Hg, and with a gradual rise in temperature from 100° to 180° C, through high efficiency fractionating columns (diameter 100 mm, reflux ratio 3 : 1). As is shown below, this purification operation is however unsuitable for industrial scale operation.

73 kg of the 60% strength crude material mentioned give, after a distillation time of 20 hours, only 34 kg of 1,2-dimethyl-tetrahydropyrimidine (throughput: 1.7 kg/hour) of 98 – 99% purity, so that the yield for the total reaction batch is about 87.5 kg or 39% of theory. The water content of the freshly prepared cyclic amidine is still 1 – 1.5%, so that if the tetrahydropyrimidine stands for a prolonged period, gradual hydrolysis with ring opening again takes place. The above refining distillation additionally leaves about 25 kg of unusable residue, representing 33 of the 60% strength crude material.

The examples which follow relate to the process according to the invention.

EXAMPLE 2

176 kg (2 kmols) of N-methyl-propylenediamine were added over the course of 3 hours to 260 kg (2 kmols) of acetoacetic acid ethyl ester and 80 kg of toluene whilst cooling with cold water (20° – 30° C). The water produced during the condensation is removed at a kettle internal temperature of at most 40° C, and 20 mm Hg. The condensate which runs into a separating container is cooled to 8° – 10° C so that good and rapid separation of the two phases is achieved. In this way 35 kg of water (representing 97% of theory) can be removed over the course of 10 hours. After completion of the azeotropic vacuum distillation, the toluene/ethyl acetate mixture is rapidly distilled off under normal pressure through a 1 m column surmounting the apparatus until the kettle internal temperature is about 135° C. The subsequent working up of the residue by distillation gives, in a simple manner, 190 kg of 1,2-dimethyl-tetrahydropyrimidine of 98 – 99% purity (boiling point$_{20}$ = 82°–85° C, $n_D^{20}$ = 1.4905).

Yield: 85% of theory.

The unusable residue amounts to about 30 kg.

EXAMPLE 3

130 kg (1 kmol) of acetoacetic acid ethyl ester are added to a mixture of 156 kg (1 kmol) of N-cyclohexyl-propylenediamine, 120 kg of toluene and 53 kg of anhydrous sodium carbonate whilst stirring and keeping the reaction temperature at 25° – 30° C by water cooling. Since the condensation of the acetoacetic acid ester with N-cyclohexyl-propylenediamine takes place at a sufficient reaction velocity at room temperature, the sodium carbonate, which now contains water, can be filtered off after merely 10 hours. The solvent, toluene, and the ethyl acetate already present are distilled off at a kettle temperature of 130° – 140° C under normal pressure. The residue which remains can subsequently be worked up in a high vacuum, using a fractionating column, whereby 126 kg (75% of theory) of 1-cyclohexyl-2-methyltetrahydropyrimidine are obtained in 96% purity. (Boiling point$_{0.8}$ = 110° – 115° C, $n_D^{20}$ = 1.5132).

EXAMPLES 4 TO 11

Following the process indicated in Example 3, further 1-substituted 2-methyltetrahydropyrimidines, shown below, were prepared from the corresponding N-substituted propylenediamines and acetoacetic acid ethyl ester.

| Example No. | Compound: | Boiling point or melting point | Yield |
| --- | --- | --- | --- |
| 4 | 1-Hydroxyethyl-2-methyl-tetrahydropyrimidine | b.p.$_{0.1}$:131–137° C<br>m.p.: 72–74° C | 75% |
| 5 | 1-Butyl-2-methyl-tetrahydropyrimidine | b.p.$_{12}$:108–110° C | 91% |
| 6 | 1-(2-Ethylhexyl)-2-methyl-tetrahydropyrimidine | b.p.$_{0.1}$:105–108° C | 85% |
| 7 | 1-Dodecyl-2-methyl-tetrahydropyrimidine | b.p.$_{0.1}$:156–159° C | 86% |
| 8 | 1-(1-Methyl-cyclohexyl)-2-methyl-tetrahydropyrimidine | b.p.$_{0.1}$:104–106° C | 88% |
| 9 | 1-(2-Methylhexyl)-2-methyl tetrahydropyrimidine | b.p.$_{0.1}$:86–90° C | 65% |
| 10 | 1-(3,3-Dimethyl-5-methyl-cyclohexyl)-2-methyl-tetrahydropyrimidine | b.p.$_{0.1}$:86–90° C | 67% |
| 11 | 1-Benzyl-2-methyl-tetrahydropyrimidine | b.p.$_{0.1}$:150–153° C<br>m.p.: 40–43° C | 87% |

EXAMPLE 12

A mixture of 213 g (1 mol) of acetoacetic acid N-dibutylamide, 200 ml of toluene, 50 g of barium oxide and 88 g of N-methyl-propylenediamine was stirred for 5–6 hours at room temperature. After filtering off the Ba(OH)$_2$.xH$_2$O the solvent, toluene, is distilled off under normal pressure whilst gradually raising the reaction temperature to 140° – 150° C. On fractional distillation of the residue in vacuo, 68.5 g of 1,2-dimethyl-tetrahydropyrimidine of boiling point$_{12}$:78° – 84° C (61% of theory) and 115 g of acetic acid N-dibutylamide (boiling point$_{12}$: 115° – 120° C) are obtained.

EXAMPLE 13

Analogously to Example 12, 183 g (1 mol) of acetoacetic acid N-cyclohexylamide and 88 g of N-methyl-propylenediamine gave, by the method according to Example 4, 35 g of 1,2-dimethyl-tetrahydropyrimidine (81% of theory) and 80 g of acetic acid N-cyclohexylamide (boiling point$_{0.1}$: 130°–133° C).

What is claimed is:

1. Process for preparing 1-substituted, 2-methyltetrahydropyrimidine which comprises reacting an N-substituted propylene diamine with an acetoacetic acid ester or amide at a temperature of from 0° to 80° C, and removing the water produced in the reaction at a temperature of from 0° to 80° C.

2. Process for preparing of 1-substituted, 2-methyltetrahydropyrimidine of the general formula

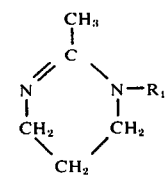

wherein
R$_1$ is a straight-chain, branched-chain or cyclic, saturated, unsaturated or aromatic, optionally substituted hydrocarbon radical with from 1 to 17 carbon atoms
which comprises reacting an N-substituted propylenediamine of the general formula

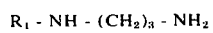

wherein
R$_1$ has the abovementioned meaning with an acetoacetic acid derivative of the general formula

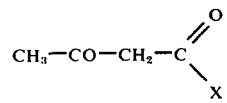

wherein
X is -OR$_2$, -NHR$_2$ or -N(R$_2$)$_2$ and
R$_2$ is an optionally substituted aryl, alkyl or cycloalkyl radical with 1 to 17 carbon atoms at a temperature of from 0° to 80° C, and removing the water produced in the reaction at a temperature of from 0° to 80° C.

3. Process of claim 2 wherein the reaction is carried out in the absence of a catalyst.

4. Process of claim 2 wherein the reaction is carried out in the presence of an inert solvent.

5. Process of claim 2 wherein the water produced in the reaction is removed by adding an inert dehydrating agent.

6. Process of claim 2 wherein the water produced in the reaction is removed by azeotropic distillation.

7. Process of claim 2 wherein the reaction and the removal of water are conducted at temperatures of from 20° to 50° C.

* * * * *

UNITED STATES PATENT AND TRADEMARK OFFICE
CERTIFICATE OF CORRECTION

PATENT NO. : 4,001,232
DATED : January 4, 1977
INVENTOR(S) : Gerhard Groegler et al It is certified that error appears in the above-identified patent and that said Letters Patent are hereby corrected as shown below:

In the abstract, line 3, "amine" should read -- amide --.

Signed and Sealed this

Fifth Day of April 1977

[SEAL]

Attest:

RUTH C. MASON
Attesting Officer

C. MARSHALL DANN
Commissioner of Patents and Trademarks